(12) United States Patent
McElroy et al.

(10) Patent No.: US 11,446,448 B2
(45) Date of Patent: Sep. 20, 2022

(54) NEEDLE SAFETY SYSTEM

(71) Applicant: West Pharmaceutical Services, Inc., Exton, PA (US)

(72) Inventors: Terry McElroy, Bray (IE); Colin Dowling, Dublin (IE); Patrick Dowling, Dublin (IE); Martin McGarry, Dublin (IE)

(73) Assignee: West Pharmaceutical Services, Inc., Exton, PA (US)

( * ) Notice: Subject to any disclaimer, the term of this patent is extended or adjusted under 35 U.S.C. 154(b) by 80 days.

(21) Appl. No.: 16/637,418

(22) PCT Filed: Aug. 13, 2018

(86) PCT No.: PCT/US2018/046492
§ 371 (c)(1),
(2) Date: Feb. 7, 2020

(87) PCT Pub. No.: WO2019/033100
PCT Pub. Date: Feb. 14, 2019

(65) Prior Publication Data
US 2020/0179614 A1   Jun. 11, 2020

Related U.S. Application Data

(60) Provisional application No. 62/544,202, filed on Aug. 11, 2017.

(51) Int. Cl.
*A61M 5/32* (2006.01)
*F16B 21/18* (2006.01)

(52) U.S. Cl.
CPC ........ *A61M 5/3271* (2013.01); *A61M 5/3202* (2013.01); *A61M 5/326* (2013.01);
(Continued)

(58) Field of Classification Search
CPC .............. A61M 5/3721; A61M 5/3271; A61M 5/3202; A61M 5/3272; A61M 5/3213;
(Continued)

(56) References Cited

U.S. PATENT DOCUMENTS

| 4,644,941 A | 2/1987 | Ogle, II |
| 4,915,697 A | 4/1990 | DuPont |

(Continued)

FOREIGN PATENT DOCUMENTS

| DE | 102015110343 A1 | 12/2016 |
| FR | 3037807 A1 | 12/2016 |

(Continued)

OTHER PUBLICATIONS

Int'l Search Report and Written Opinion dated Nov. 27, 2018 in Int'l Application No. PCT/US2018/046468.
(Continued)

*Primary Examiner* — Nilay J Shah
*Assistant Examiner* — Robert F Allen
(74) *Attorney, Agent, or Firm* — Blank Rome LLP (57) ABSTRACT

A syringe safety system may include a sleeve. The sleeve may include a guide track formed in the sleeve. The guide track may have a guide pin retention portion, a travel portion, and a lockout portion. The syringe safety system may include a collar having a guide pin extending radially from an exterior surface of the collar. A spring may extend between and be coupled to the collar and the sleeve. A cap may engage the sleeve. The cap may be configured to retain the guide pin in the guide pin retention portion of the guide tack. When the cap is removed, the spring advances the guide pin into the travel portion of the guide track.

21 Claims, 10 Drawing Sheets

(52) U.S. Cl.
CPC ........ *A61M 5/3213* (2013.01); *A61M 5/3272* (2013.01); *A61M 5/3293* (2013.01); *F16B 21/186* (2013.01); *A61M 2005/3267* (2013.01)

(58) Field of Classification Search
CPC ................ A61M 5/326; A61M 5/3293; A61M 2005/3267; A61M 5/3204; F16B 21/186
See application file for complete search history.

(56) References Cited

U.S. PATENT DOCUMENTS

| | | | |
|---|---|---|---|
| 4,966,592 A | 10/1990 | Burns et al. | |
| 5,536,047 A | 7/1996 | Detable et al. | |
| 5,964,731 A * | 10/1999 | Kovelman | A61M 5/3271 604/110 |
| 10,335,552 B2 | 7/2019 | Grosser | |
| 2007/0256827 A1 * | 11/2007 | Guerrero | E21B 33/134 166/207 |
| 2009/0324327 A1 | 12/2009 | McAndrews et al. | |
| 2010/0185178 A1 | 7/2010 | Sharp et al. | |
| 2015/0190586 A1 | 7/2015 | Takemoto | |
| 2015/0246182 A1 * | 9/2015 | Evans | A61M 5/326 604/198 |
| 2016/0174960 A1 | 6/2016 | Albrecht et al. | |
| 2017/0172848 A1 | 6/2017 | Goodman et al. | |
| 2018/0147366 A1 | 5/2018 | Aneas | |
| 2018/0177955 A1 * | 6/2018 | Aneas | A61M 5/3272 |

FOREIGN PATENT DOCUMENTS

| | | |
|---|---|---|
| JP | 2012525200 A | 10/2012 |
| WO | 2010126432 A1 | 11/2010 |
| WO | 2016091554 A1 | 6/2016 |
| WO | 2016158627 A1 | 10/2016 |
| WO | 2016202498 A1 | 12/2016 |
| WO | 2016202614 A1 | 12/2016 |
| WO | 2016202670 A1 | 12/2016 |
| WO | 2017012833 | 1/2017 |

OTHER PUBLICATIONS

Int'l Preliminary Report on Patentability dated Aug. 28, 2019 in Int'l Application No. PCT/US2018/046468.
Int'l Search Report and Written Opinion dated Oct. 31, 2018 in Int'l Application No. PCT/US2018/046508.
Int'l Preliminary Report on Patentability dated Nov. 11, 2019 in Int'l Application No. PCT/US2018/046508.
Int'l Preliminary Report on Patentability dated Oct. 23, 2019 in Int'l Application No. PCT/US2018/046492.
Int'l Search Report and Written Opinion dated Oct. 27, 2018 in Int'l Application No. PCT/US2018/046492.

* cited by examiner

NEEDLE SAFETY SYSTEM

CROSS-REFERENCE TO RELATED APPLICATIONS AND INCORPORATION BY REFERENCE

This application is a section 371 of International Application No. PCT/US2018/046492, filed Aug. 13, 2018, which was published on Feb. 14, 2019 under International Publication No. WO 2019/033100 A1, and which claims priority to U.S. Provisional Patent Application No. 62/544,202, filed Aug. 11, 2017, the entire contents of each of which is incorporated herein by reference in its entirety.

BACKGROUND

Needlestick injuries are an occupational hazard for healthcare workers. Unintended needlesticks have the potential for transmitting blood-borne viruses such as hepatitis B and C and the human immunodeficiency virus (HIV) to the recipient. After a needlestick injury, certain procedures must be followed to minimize the risk of infection for the recipient, such as laboratory blood tests and post-exposure prophylaxis started immediately after exposure to a pathogen, such as one of the aforementioned viruses, in order to prevent infection by the pathogen and the development of the associated disease.

The risk of needle stick injuries increases when medicines are administered in a non-hospital or medical care facility environment. This is often the case when vaccines and other necessary medicines are administered in the field or in an emergency.

Safety devices have been used to reduce the frequency of post-injection needlesticks. Some safety device may be used to cover, or shield, the needle after injection. Some safety devices may automatically deploy a sheath around the needle as soon as it is withdrawn from the patient. Because the sheath is deployed automatically, the needle is never exposed or is exposed only for a negligible period. This reduces the risk of needlestick injuries. The sheath may include a sleeve that acts to cover the needle of the syringe. Such safety devices may be removed from the syringe after use, in which case a contaminated needle may be re-exposed and a renewed risk of needle stick injury presents itself.

SUMMARY

A needle safety system that is tamper-evident is described. It may include a sleeve. A guide track may be formed in the sleeve. In some embodiments, the guide track may be formed on an inner surface of the sleeve. The guide track may have one or more portions. In some embodiments, the guide track may have a pin retention portion, a travel portion, and a lockout portion. A needle safety system may also include a collar. In some embodiments, the collar is inside the sleeve. The collar may include a guide pin radially extending from an exterior surface of the collar. A spring may couple to the collar and the sleeve. In some embodiments, the spring may be a torqueable compression springe. A cap may be configured to retain the guide pin in the pin retention portion of the guide track. When the cap is removed, the spring advances the guide pin from the pin retention portion of the guide track to the travel portion of the guide track.

According to some embodiments, the lockout portion and the guide pin retention portions are on opposite sides of the travel portion of the guide track. The sleeve may have a cap seat configured to receive the cap. The cap may include a guide pin retention member that extends from the surface of the cap. This guide pin retention member may be configured to enter the pin retention portion of the guide track to prevent or limit the movement of the guide pin.

According to some embodiments, the collar has an inner and an outer collar. The inner collar is rotatably coupled to the outer collar. The guide pin extends from the outer collar. The outer collar may also have an accordion portion configured to flex under rotational stress. The accordion portions may relieve stresses imparted to the outer collar by the spring, which may be a torsional spring. The inner and the outer collars may engage with each other via a snap fit connection.

The sleeve of a system according to some embodiments may include a second guide track formed in the sleeve. Like the first guide track, the second guide track may have a guide pin retention portion, travel portion, and lockout portion. The first and the second guide tracks may be formed on opposite sides of the sleeve. Both may be formed on an internal surface of the sleeve. A sleeve with two guide tracks may be configured to work with a collar that has a second guide pin. The first guide pin is configured to engage the first guide track and the second guide pin is configured to engage the second guide track.

A sleeve for a needle safety system may include a cylindrical portion that has a distal and a proximal end. A guide track may be formed in the cylindrical portion. The guide track may have a pin retention portion, a travel portion, and a lockout portion. The pin retention portion may open at the proximal end of the cylindrical portion. The lockout portion and the guide pin retention portion may be on opposite sides of the travel portion of the guide track.

The lockout portion may include a channel portion and a capture portion. The channel portion may extend from the travel portion and the capture portion may extend from the channel portion. The capture portion may include a guide pin block that is configured to retain the guide pin inside the capture portion. The cylindrical portion may include a longitudinal axis extending between the distal end and the proximal end of the cylindrical portion and the travel portion of the guide track may be parallel to this longitudinal axis. The guide pin retention portion of the guide track may have a channel configured to receive a guide pin retention member.

The sleeve may be produced from two portions. The portions may be formed from an injection molding process.

A syringe system may include a syringe having a proximal and a distal end. The syringe may have a syringe hub at the distal end. A cannula may extend from the syringe hub. A multi-part collar may be coupled to the syringe hub. The multi-part collar may have an inner and an outer collar. The inner and the outer collar may be rotatably coupled. A guide pin may extend from the surface of the outer collar. The guide pin may engage with a guide track formed in a cylindrical sleeve. The guide track may have a pin retention portion, a travel portion, and a lock out portion. A torqueable compression springe may be coupled to the cylindrical sleeve and the outer collar. A cap may have a guide pin retention member. The guide pin may be located in the guide pin retention portion and may abut the guide pin retention member. The cylindrical sleeve may extend over the cannula when the guide pin is in the guide pin retention portion of the guide track.

DESCRIPTION OF THE DRAWINGS

The disclosure will be readily understood by the following detailed description in conjunction with the accompanying drawings, wherein like reference numerals designate like structural elements, and in which.

DETAILED DESCRIPTION

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents within the spirit and scope of the described embodiments as defined by the claims.

An injection device with a needle safety system may have a barrel to hold a medicine. The barrel may have a hub from which a cannula, or needle, extends. A collar may be seated on or coupled to the hub. The collar may be configured to rotate relative to the hub. The collar may have a guide pin extending from the surface of the collar. The guide pin may be configured to engage a guide track formed in a sleeve. The sleeve may extend over the cannula when the guide pin is located in some portions of the guide track and the sleeve may be retracted to expose the cannula when the guide pin is located in certain portions of the guide track. In some embodiments, the guide pin is only able to move in certain directions within the guide track. The sleeve may also rotate relative to the collar as the guide pin advances in the guide track.

Figure 1:
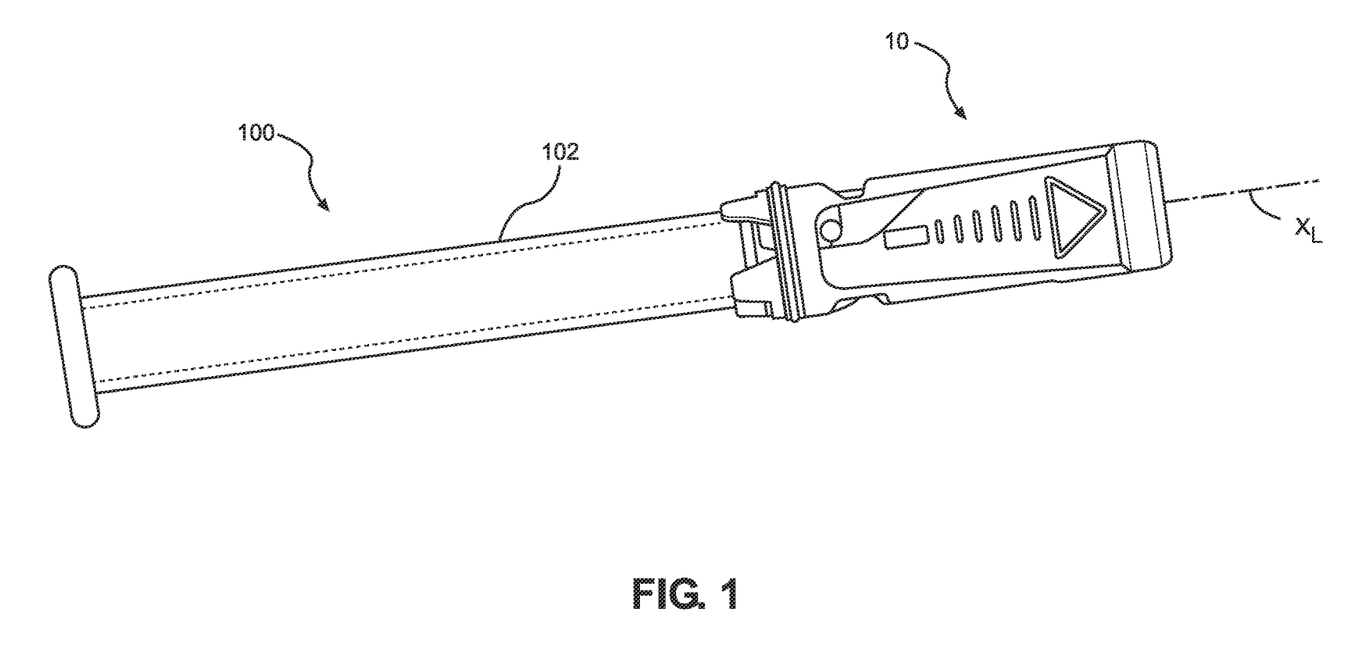
FIG. 1 shows a needle safety system assembled onto a syringe.

FIG. 1 shows an injection device 100 with a barrel 102 and a needle safety system 10 according to some embodiments. Injection device 100 may be a pharmaceutical syringe. Injection device 100 may be pre-filled with a medicament (not shown) or may be provided without a medicament for filling by a user. Injection device 100 may have a generally cylindrical barrel 102 extending along a longitudinal axis $X_L$.

Figure 2:
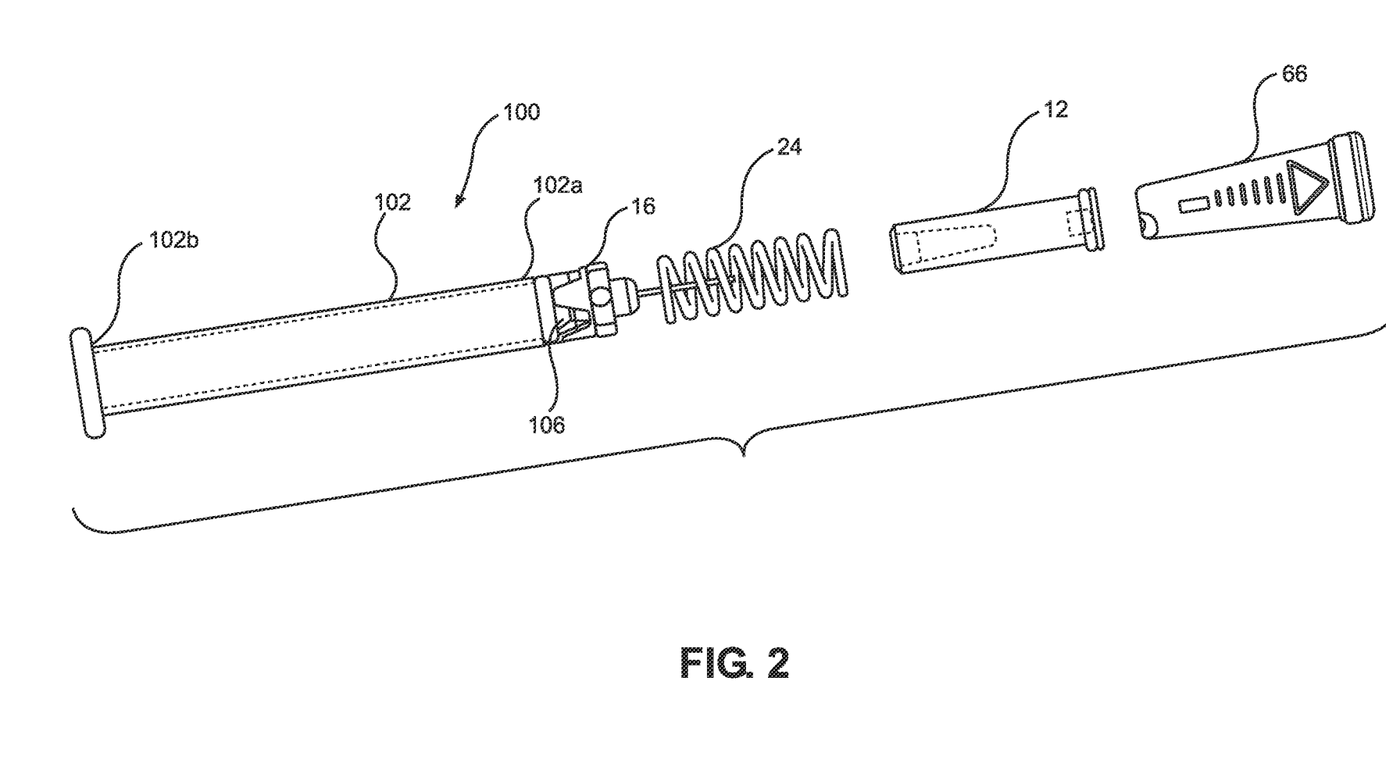
FIG. 2 shows an exploded view of a needle safety system assembled onto a syringe.

FIG. 2 shows an exploded view of an injection device 100 with a needle safety system 10. As shown in FIG. 2, barrel 102 has a distal end 102a and an opposing proximal end 102b. Barrel 102 may be formed of nearly any material capable of safely enclosing medicaments. For example, barrel 102 may be formed of glass or polymeric material. The distal end 102a of the barrel 102 has a barrel shoulder 104 (see FIG. 10) from which a hub 106 extends. Hub 106 has a radially outwardly-extending, proximally-facing, distal-hub annular shoulder 108 (FIG. 10) spaced from the barrel shoulder 104 and a radially outwardly-facing distal-hub surface 110 (FIG. 10) between barrel shoulder 104 and distal-hub annular shoulder 108.

A cannula 112 (FIG. 10), or needle, extends distally from the hub 106. Cannula 112 is in fluid communication with a bore (not shown) of the barrel 102. Cannula 112 may be removably attached to the hub 106. Alternatively, and preferably, the cannula 112 may be fixedly attached thereto. A piston (not shown) is slidably receivable in the bore of the barrel 102 is attached to a piston rod (not shown) having a free proximal end that extends from the proximal end 102b of the barrel 102. A sleeve 12, within which barrel 102 is moveable, at least partially encloses cannula 112.

FIG. 2 also shows a multi-part collar 16 disposed in the sleeve 12. As explained below, and with reference to FIGS. 9 and 10, the multi-part collar 16 comprises an inner collar 18 fixedly attachable to the hub 106 and an outer collar 20 rotatably attached to the inner collar 18 about a rotational axis. At least one guide pin 22 extends radially outwardly from the outer collar 20. In some embodiments, two guide pins 22 extend outwardly from the outer collar 20 on opposite sides thereof. Details of the structure of the multi-part collar 16 are discussed in more detail below. Multi-part collar 16 is enclosed by sleeve 12.

A spring 24 is also enclosed in sleeve 12. Spring 24 is coupled to outer collar 20 and sleeve 12. Spring 24 may be torsional, torqueable, and compressible. Spring 24 biases sleeve 12 in the distal direction to cover cannula 112. Spring 24 also rotationally biases guide pin 22, as explained in more detail below. A cap 66 is configured to cover the distal end of sleeve 12. In some embodiments, cap 66 engages sleeve 12 using a friction fit connection or a snap-fit connection.

Figure 3A:
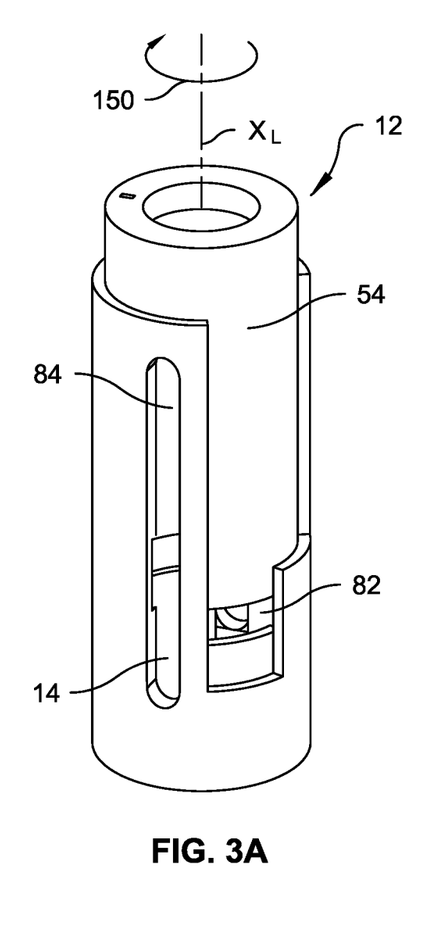
FIG. 3A shows a perspective view of a sleeve of a needle safety system.
Figure 3B:
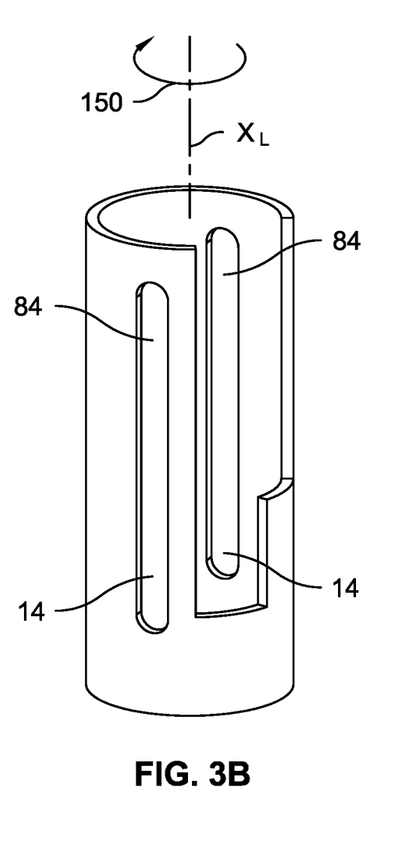
FIG. 3B shows a perspective view of an outer portion of the sleeve shown in FIG. 3A.
Figure 3C:
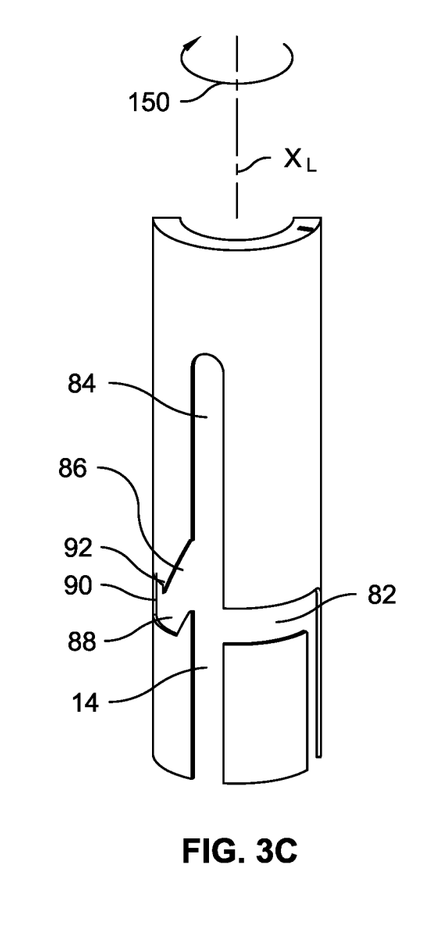
FIG. 3C shows a perspective view of half of an inner portion of the sleeve shown in FIG. 3A.

Referring to FIGS. 3A-3C, at least one guide track 14 is formed in the sleeve 12. In some embodiments, two identical guide tracks 14 are formed in the sleeve 12 on opposite sides thereof. FIG. 3A shows a perspective view of sleeve 12 according to some embodiments with guide track 14 formed therein. As shown in FIGS. 3B and 3C, portions of the guide track 14 may form a channel into the inner surface of the sleeve 12 at a depth not extending through the entire thickness of the sleeve 12, and portions of the guide track 14 may form a channel through the entire thickness of the sleeve 12. As assembled, the movement of guide pin 22 is limited by the surfaces forming the boundaries of the guide track 14. That is, guide pin 22 can only move within guide track 14.

As mentioned above, spring 24 extends between the outer collar 20 and the sleeve 12. In some embodiments, spring 24 may be a torqueable compression spring. In addition to biasing sleeve 12 in the distal direction, spring 24 rotationally biases the outer collar 20 relative to the sleeve 12. When guide pin 22 is located in guide track 14, as further explained below, guide pin 22 is also rotationally biased relative to sleeve 12. The shape of guide track 14 can take advantage of the bias in the movement of guide pin 22 to advance guide pin 22 through guide track 14.

FIGS. 3A-3C show several portions of guide track 14. FIGS. 3A-3C also show guide pin biasing direction 150. Guide pin biasing direction 150 is the direction in which spring 24 biases guide pin 22. As shown in FIG. 3C, guide track 14 has three main portions. Guide pin retention portion 82 extends from a proximal end of sleeve 12 to travel portion 84. Travel portion 84 is straight and is oriented parallel to longitudinal axis $X_L$. However, travel portion 84 can have different shapes or configurations. Lockout portion 86 of guide track 14 is located in guide pin biasing direction 150 relative to travel portion 84. Lockout portion 86 is configured to capture guide pin 22 as cannula 112 is withdrawn after injection. Lockout portion 86 has a lockout channel 88 and a lockout area 90. A guide pin block 92 extends from the distal end of lockout area 90 and is configured to interfere with guide pin 22 to prevent guide pin 22 from exiting lockout area 90. Guide pin retention portion 82 may also be configured to receive guide pin 22 during assembly. Guide pin retention portion 82 may extend to a proximal edge of sleeve 12 such that guide pin 22 may slide into guide pin retention portion 82 during assembly. Guide pin retention portion 82 and lockout portion 86 may be on opposite sides of travel portion 84. For example, as guide pin 22 travels from guide pin retention portion 82 to lockout portion 86, it must necessarily travel through travel portion 84. Travel portion 84 may be in the guide pin biasing direction 150 relative to guide pin retention portion 82, and lockout portion 86 may be in the guide pin biasing direction 150 relative to travel portion 84.

Figure 4A:
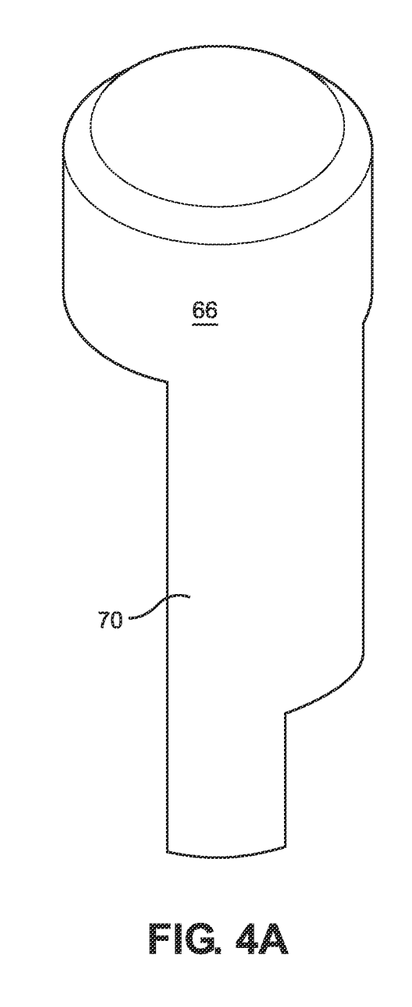
FIGS. 4A-4B show a cap of a needle safety system.
Figure 4B:
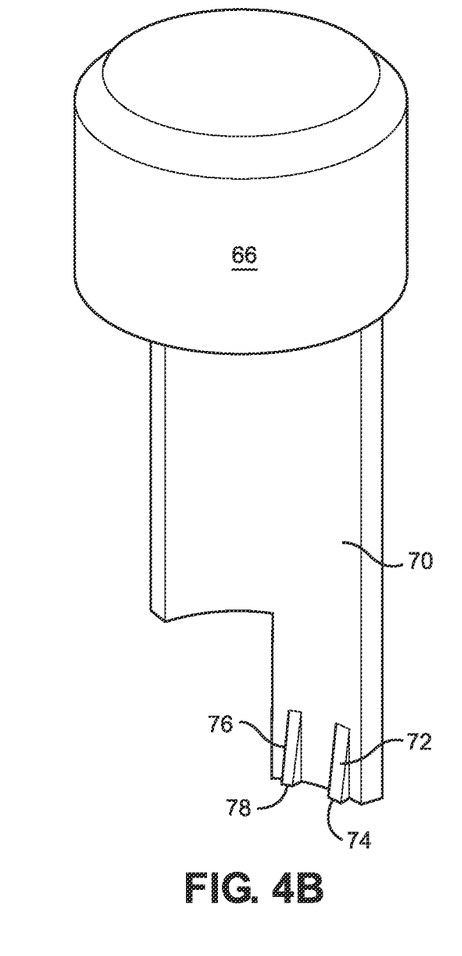

FIGS. 4A and 4B show the cap 66. The cap 66 includes a portion 70, which is configured to engage a cap seat 54 (FIG. 3A) of the sleeve 12. Cap seat 54 and cap 66 may engage using a snap fit or a friction fit connection. Cap seat 54 may be in the form of a recess formed in sleeve 12. The recess may be shaped to receive the portion 70 of the cap 66. Although FIG. 3B shows the cap seat 54 being separate from the travel portion 84, in some embodiments the cap seat 54 may extend over the travel portion 84. Cap 66 may also have a tamper rib 72 and a retention rib 76, both extending from an inner wall of cap 66. Both of the tamper and retention ribs 72 and 76 may be wedge shaped, each having a proximal flat surface 74, 78 perpendicular to the longitudinal axis $X_L$. The tamper and retention ribs 72, 76 may each taper distally from the flat surface 74, 78 toward the inner surface of the cap 66. The taper of the tamper and retention ribs 72, 76 may permit the cap to be removed easily. The tamper rib 72 may be configured to align and engage with the travel portion 84 of the sleeve 12 and the retention rib 76 may be configured to engage with the retention portion 82 of the sleeve 12.

Figure 5A:
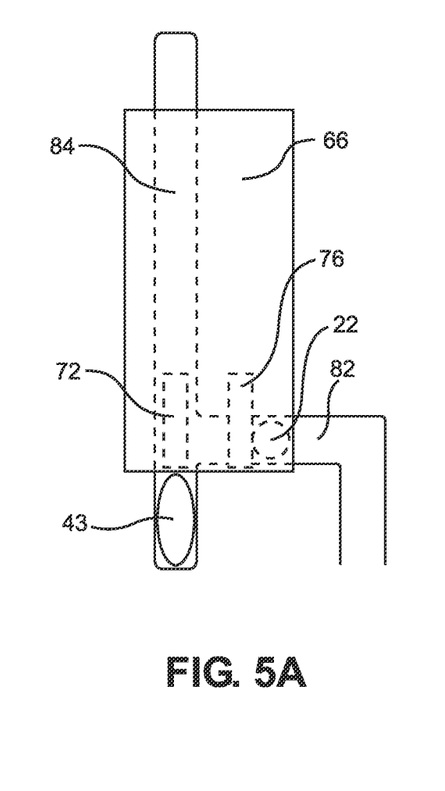
FIGS. 5A-5C show schematic diagrams of various configurations of a needle safety system in different states of operation.
Figure 5B:
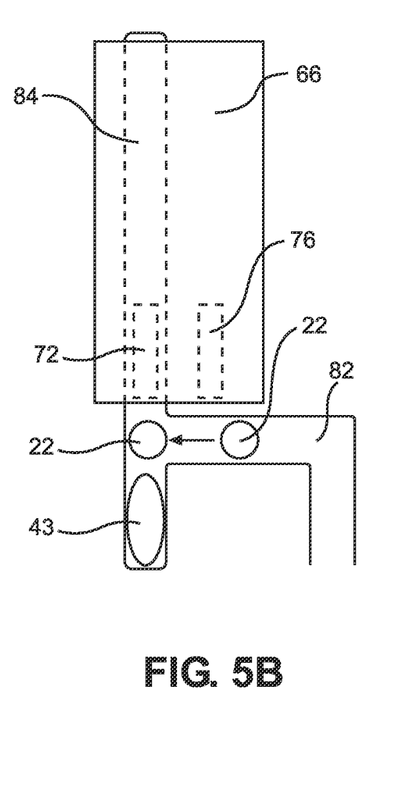
Figure 5C:
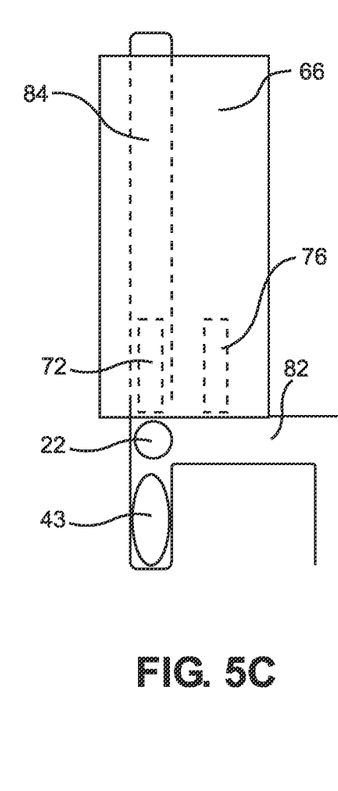

FIGS. 5A-5C show the relative position of the tamper and retention ribs 72, 76 when the cap 66 is positioned onto the sleeve 12 at various stages of operation of the needle safety device 10. For example, FIG. 5A shows a relative configuration of the cap 66 and sleeve 12 before use. The guide pin 22 is located in guide pin retention portion 82 and is prevented from advancing into travel portion 84 by the retention rib 76. However, as shown in FIG. 5B, once a user at least partially removes cap 66, the retention rib 76 is removed from guide pin retention portion 82 and guide pin 22 advances, under the rotational biasing of spring 24, to travel portion 84 of guide track 14. Once the retention rib 76 has released guide pin 22, guide pin 22 cannot move back into guide pin retention portion 82 because spring 24 prevents movement of guide pin 22 in a direction opposite to guide pin biasing direction 150. As shown in FIG. 5C, if the cap 66 were to be placed back onto the sleeve 12 at this point, while the guide pin 22 is in the travel portion 84, the flat surface 74 of the tamper rib 72 would abut the guide pin 22, thereby preventing the cap 66 from seating correctly in the cap seat 54. Moreover, even if the cap 66 were to be forced into the cap seat 54, the tamper rib 72 would then sit on top of the guide pin 22 indicating to a user that the cap 66 had been previously removed. Removal of the cap 66 may also provide tactile or auditory feedback to alert the user that the guide pin 22 has advanced. In addition to, or alternatively to, the tamper prevention features associated with the tamper rib 72 as discussed above, if the user does not feel or hear this feedback, the user may believe that the cap has already been removed and that the sterility of the needle could be compromised.

The cap 66 can have a base which is generally cylindrical, and a button which fits on one end. Cap 66 can also house a needle shield (not shown). The needle shield can be shaped such that it can pass through the base of the cap and be held in position by the dimension of the cap. A button can be attached to the base of the cap to cover the end of the needle shield.

Figure 6A:
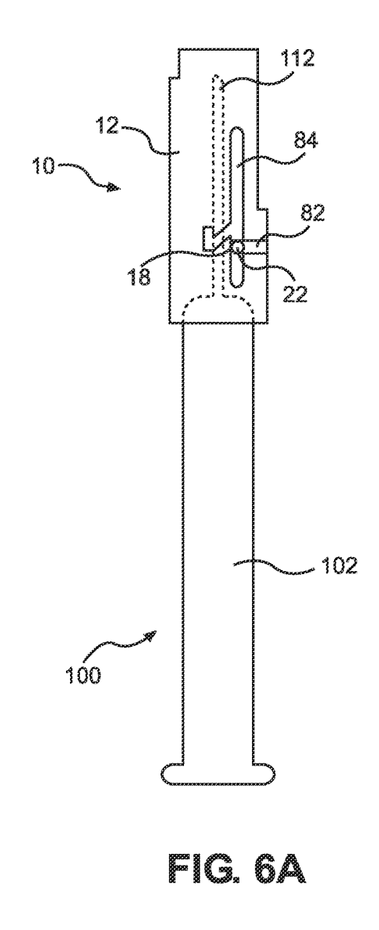
FIGS. 6A-6C show a needle safety system on a syringe in different states of operation.
Figure 6B:
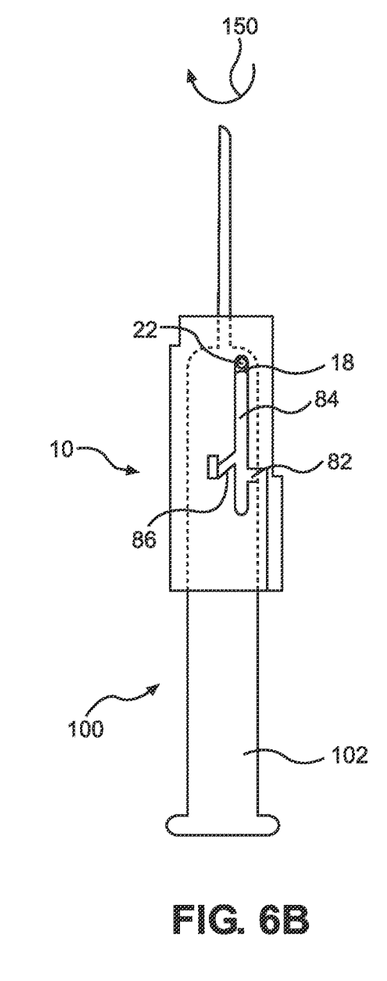
Figure 6C:
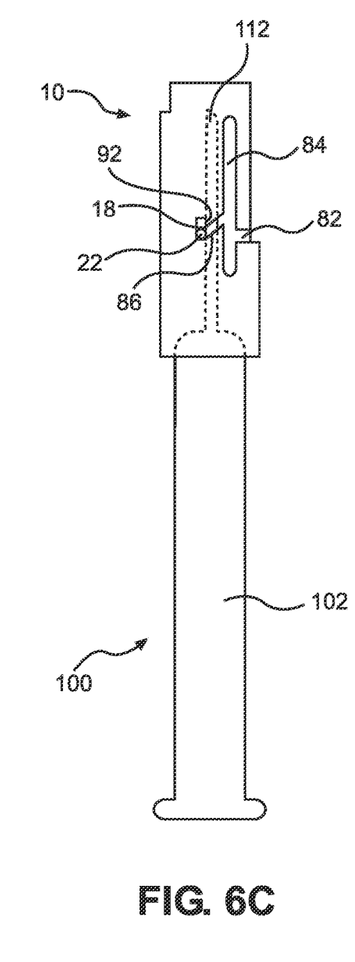

FIGS. 6A-6C show an injection device 100 with needle safety system 10. Although cannula 112, portions of barrel 102, guide track 14, and guide pin 22 would be obscured by sleeve 12 in various stages of operation, they are shown in FIGS. 6A-6C in phantom to show the operation of needle safety system 10.

FIG. 6A shows needle safety system 10 after cap 66 has been removed. Once cap 66 is removed, the retention rib 76 no longer protrudes into guide track 14 and no longer interferes with guide pin 22. Thus, guide pin 22 is permitted to advance in guide track 14. The forces imparted by spring 24 on collar 16 and sleeve 12 rotate collar 16 relative to sleeve 12. This torsional force from spring 24 advances guide pin 22 in guide track 14 in the guide pin biasing direction 150 into travel portion 84 of guide track 14. At this point, the injection device 100 is ready for use. In operation, the distal end of injection device 100 would be pressed against a patient (not shown). Needle safety system 10 advances proximally relative to the syringe barrel 102. As it does so, guide pin 22 advances through travel portion 84. FIG. 6B shows an injection device 100 with a syringe safety system 10 during injection. Cannula 112 is exposed so that it may pierce the patient's skin and deliver the medication. Guide pin 22 is at the distal end of travel portion 84. FIG. 6B shows that guide pin 22 remains biased in guide pin biasing direction 150 and against a wall 152 of travel portion 84. After use, the syringe is withdrawn from the patent and guide pin 22 moves along wall 152 of travel portion 84. Because of the biasing in guide pin biasing direction 150, guide pin 22 eventually moves into lockout channel 88. As shown in FIG. 6C, guide pin 22 moves into lockout area 90. The injection process is then complete. Because guide pin 22 cannot be moved back into travel portion 84, sleeve 12 cannot be withdrawn and cannula 112 remains sheathed.

Figure 7:
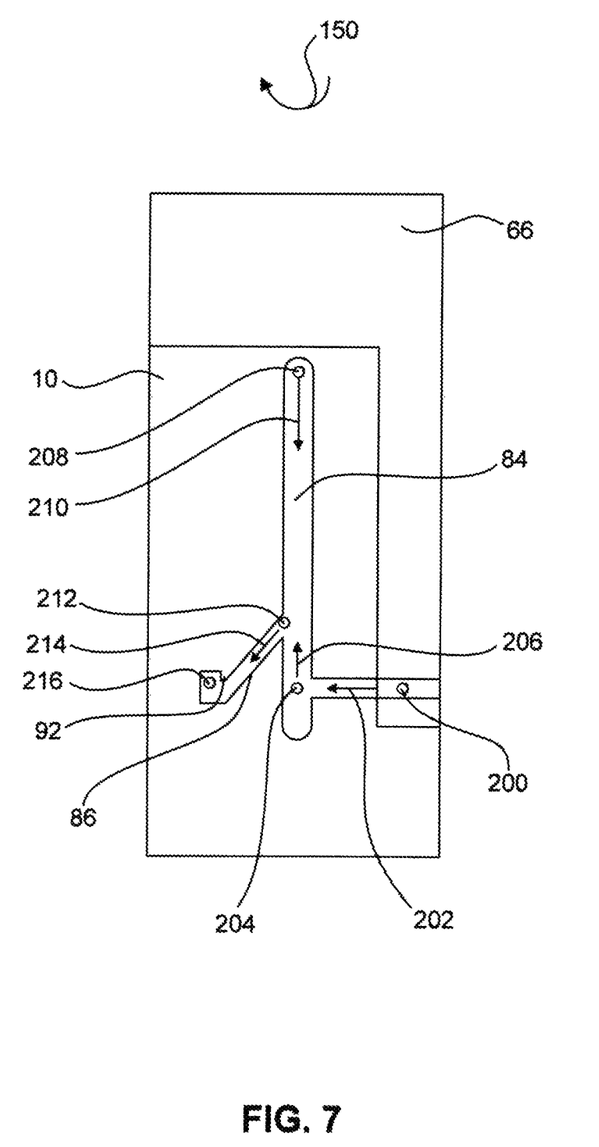
FIG. 7 shows a front view of a sleeve of a needle safety system.

FIG. 7 shows the movement of guide pin 22 through guide track 14 during operation. Guide pin 22 moves in the distal or proximal direction or in guide pin biasing direction 150. As it travels distally, the guide pin 22 does not move in a direction opposite to guide pin biasing direction 150, unless it momentarily enters the lockout channel 88 at its junction with the travel portion 84. In such a case, the angle of the lockout channel 88 and the user's insertion force would allow it to overcome the spring biasing force and leave the channel 88. Guide pin 22 begins at starting point 200 where it is retained by retention rib 76. Once retention rib 76 is removed, guide pin 22 advances along path 202 to primed position 204. During injection, guide pin 22 moves along injection path 206 in the travel portion 84 to maximum injection point 208. After injection, when the syringe is withdrawn, guide pin 22 moves along withdraw path 210 to lockout entrance point 212. As the withdraw continues, guide pin 22 enters lockout channel 88 via lockout channel path 214. After the withdrawal of syringe is complete, guide pin 22 is at lockout position 216 in lockout area 90.

Figure 8:
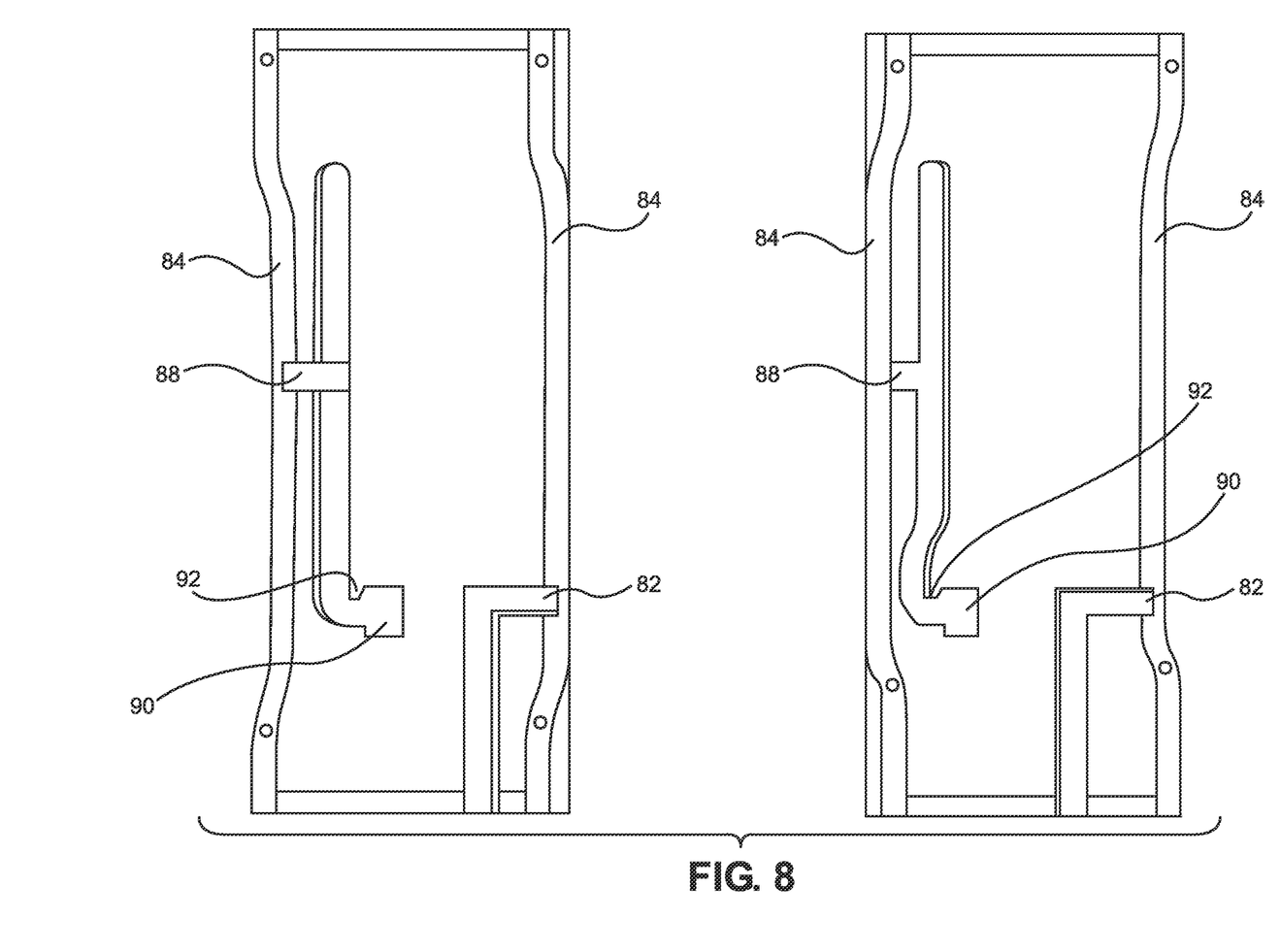
FIG. 8 shows portions of a sleeve of a needle safety system.

Sleeve 12 can be formed of plastic by injection molding, for example. In some embodiments, sleeve 12 may be formed from two molded components that together form sleeve 12. In some embodiments, these portions may be injection molded. FIG. 8 shows two halves of sleeve 12. Although the two halves, as shown, have a portion of each guide track 14 in it, in practice, each half would have the same guide track 14. In some embodiments not shown, the sleeve 12 may be formed of a molded inner shell (not shown) and a molded outer shell (not shown). Portions of the guide tracks 14 in the inner shell may be through-hole slots and portions of the guide track 14 in the outer shell may also be through hole slots. When the inner shell and the outer shell are assembled together, some portions of the guide track 14 may extend through both the inner and outer shell, whereas other portions of the guide track 14 may only extend through the inner shell.

Figure 9:
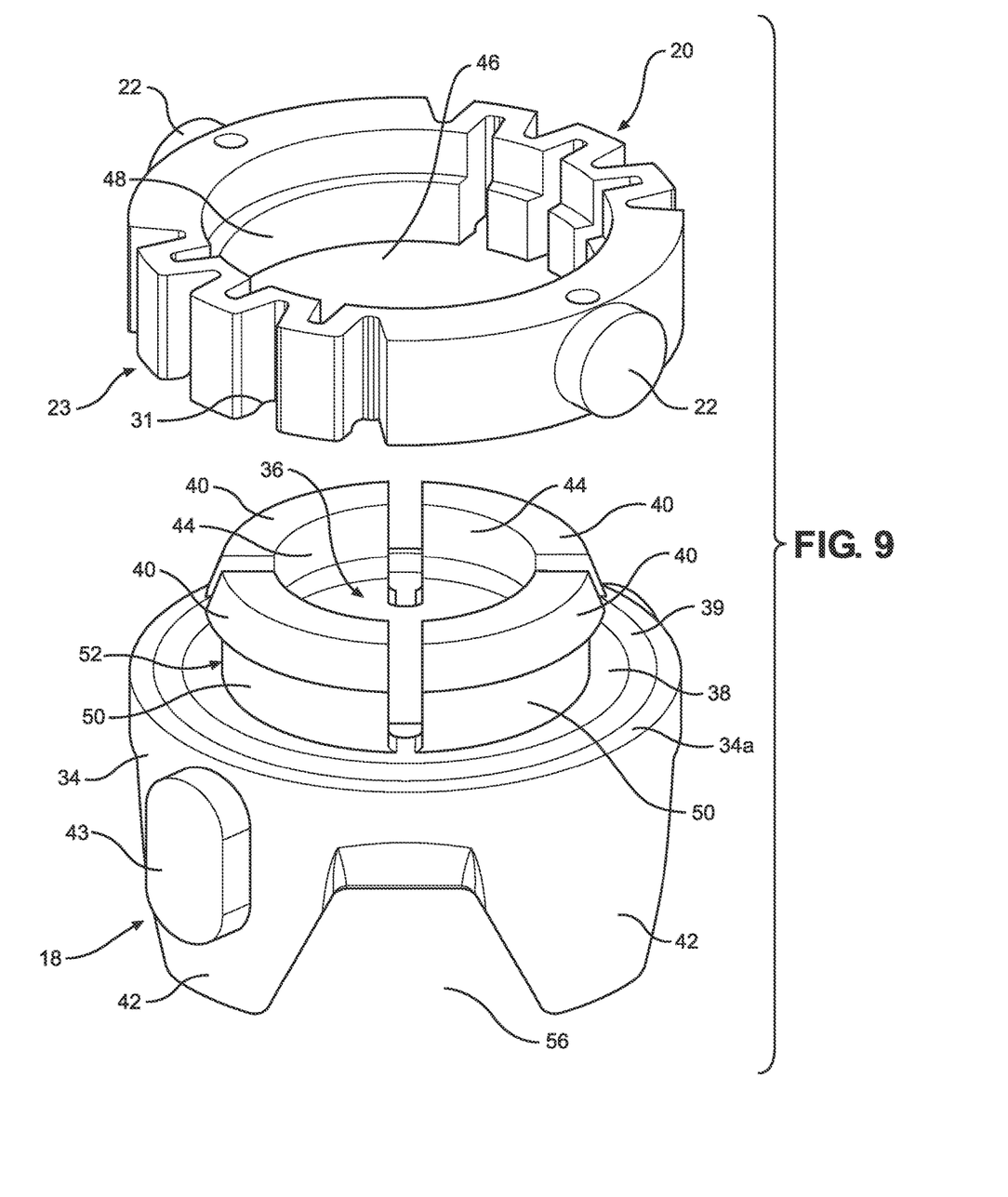
FIG. 9 shows an exploded perspective view of a collar of a needle safety system.

FIG. 9 shows multi-part collar 16. Multi-part collar 16 has an inner collar 18 fixedly attachable to the hub 106 (FIG. 10) and an outer collar 20 rotatably attached to the inner collar 18 about a rotational axis. Guide pin 22 extends radially outwardly from the outer collar 20 to slidably engage the guide track 14. In some embodiments, a pair of guide pins 22 engages corresponding guide tracks 14 in the sleeve 12.

The outer collar 20, including guide pins 22, may be comprised of a polymeric or metallic material, preferably a rigid polymer such as, for example, Acrylonitrile butadiene styrene (ABS). Moreover, the outer collar 20, including guide pins 22, may be of unitary construction. The outer collar 20 may include one or more accordion regions 23 extending in a circumferential direction and having a plurality of thin walls, which snake back and forth following a path along the circumference of the outer collar 20. The thin walls may pivot and/or flex like hinges and collectively deform to permit the accordion regions 23 to act as a spring, i.e., compress or expand in a direction other than the direction of the rotational axis and/or pivot away from or toward the rotational axis. In a preferred embodiment, the outer collar 20 has two opposed accordion regions 23, which permit the guide pins 22 to move at least radially toward and away from one another. During assembly, compression may be applied to the outer collar 20 moving the guide pins 22 toward one another to allow them to be positioned at and engage the corresponding guide tracks 14. For example, the sleeve 12 may define a proximal opening having an inner radius less than the length of each of the guide pins 22 extending from the outer collar 20 while the outer collar 20 is uncompressed. During compression, the guide pins 22 are moved to a position where they do not extend beyond the inner radius to allow them to be inserted into the sleeve 12. After the guide pins 22 have engaged the corresponding guide tracks 14, the applied compression may be removed, causing the accordion regions 23 and the guide pins 22 to return or substantially return to their previously uncompressed positions. Once assembled on the inner collar 18 and needle hub 106, the outer collar 20 is prevented from compressing, and the guide pins 22 are generally prevented from moving out of the guide tracks 14.

Figure 10:
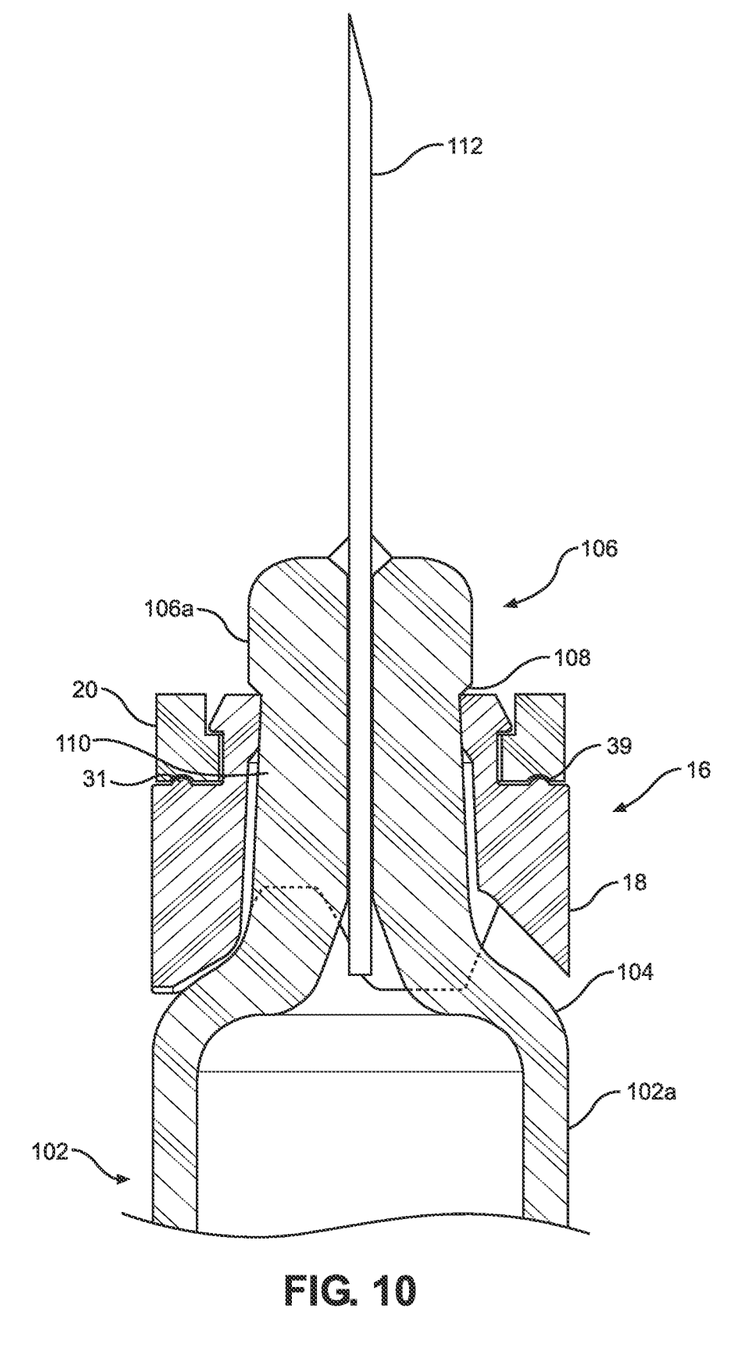
FIG. 10 shows a cross sectional view of the collar of FIG. 9 mounted on a syringe.

The inner collar 18 has a generally cylindrically-shaped base 34 with an inner-collar bore 36 extending therethrough. A distal end 34a of the inner-collar base 34 forms a radially outwardly-extending, distally-facing annular surface 38. A plurality of radially-disposed, circumferentially-spaced flexible members 40 protrude distally from the annular surface 38. In addition, a half-toroidal ring 39 extends distally from the annular surface 38 at a radially outer position with respect to the flexible members 40. A channel 50 formed in the proximal end of each flexible member 40 collectively forms a circular channel 52 circumscribing the flexible members 40. Each flexible member 40 is sufficiently compliant to allow passage of the distal end 106a of the hub 106 through the inner-collar bore 36 and to fixedly attach the inner collar 18 to the radially outwardly-facing distal-hub surface 110 by a radially inwardly-directed force applied by each flexible member 40 to the radially outwardly-facing distal-hub surface 110. A plurality of radially-disposed, circumferentially-spaced-apart legs 42 protrude proximally from the inner collar base 34. When the inner collar 18 is fixedly attached to the hub 106, the distal end of each flexible member 40 abuts the proximally-facing distal-hub annular shoulder 108 and a proximal end of each circumferentially-spaced-apart leg 42 abuts the barrel shoulder 104.

The inner collar 18 may also include one or more guide keys 43. In some embodiments, two guide keys are positioned on opposite legs 42. As shown, the guide keys 43 have an oblong shape, with a longer axis in the longitudinal direction. In some embodiments, the length of the guide keys 43 may be longer than the diameter of the guide pins 22 and longer than the entrance to the lockout channel 88. Thus, as the inner collar 18 and the outer collar 20 move distally and proximally through the travel portion 84, the guide keys 43 prevent the inner collar from leaving the travel portion 84.

In some embodiments of the inner collar 18, at least one cut-out 56 is provided between the circumferentially-spaced-apart legs 42 allowing inspection of contents inside the barrel 102.

In some embodiments of the injection device 100, the radially outwardly-facing distal-hub surface 110 has a taper. For such embodiments, an opposed radially inwardly-facing surface 44 of the distal end of each flexible member 40 preferably has a corresponding taper.

The outer collar 20 has an outer collar bore 46 and a radially inwardly-extending outer collar ring 48 that is received and freely rotatably retained in the circular channel 52 circumscribing the flexible members 40. In a preferred embodiment, the axial height of the outer collar ring 48 is less than the axial height defined by the inside of the circular channel 52. The proximal surface of the outer collar 20 defines an arc-shaped channel 31 sufficiently sized to receive the half-toroidal ring 39 from inner collar 18 when the outer collar 20 is attached to the inner collar 18. In a preferred embodiment, the radius of curvature of the arc-shaped channel 31 is larger than the radius of curvature for the half-toroidal ring 39.

The outer collar 20 is sufficiently compliant and sized to allow passage of the flexible members 40 through the outer collar bore 46 and insertion of the outer collar ring 48 in the circular channel 52 and to return to an initial outer collar configuration in which the outer collar 20 is freely rotatable in only one degree of freedom relative to the inner collar 18. The outer collar 20 may be attached to the sleeve 12 before the outer collar 20 is attached to the inner collar 18. Thus, the outer collar 20 and the sleeve 12 may be positioned together onto the inner collar 18. After the outer collar 20 has been attached to the inner collar 18, the accordion regions 23 may help permit the flexible members 40 to flex or expand radially outward when the hub 106 passes through the inner collar bore 36. Thus, as a single subassembly, the safety system 10 may be assembled onto the injection device 100.

In some embodiments, the assembled needle safety system 10 is assembled with an injection device 100, e.g., a syringe, by aligning both concentrically and applying a compression force in a linear direction to the system 10 and the syringe 100 together. The assembled needle safety system 10 and syringe 100 may then be packaged into nesting trays (not shown), e.g., one-hundred per tray. The nesting trays, having the respective assembled needle safety systems 10 and syringes 100 loaded therein, may then be delivered to an automatic syringe filling system (not shown) having filling lines, wherein a substance, e.g., a medicament, drug or other injectable medicine, is filled in the syringes 100 and respective plungers (not shown) are inserted into the syringes 100. Alternatively, the assembled needle safety systems 10 may be inserted in the nesting trays and delivered to the automatic syringe filling system. Syringes 100 may then be assembled to the needle safety systems 10, respectively, held in the nesting trays. The syringes 100 may then be filled with the substance and the plungers thereafter inserted into the syringes 100.

The foregoing descriptions of the specific embodiments described herein are presented for purposes of illustration and description. These exemplary embodiments are not intended to be exhaustive or to limit the embodiments to the precise forms disclosed. All specific details described are not required in order to practice the described embodiments.

It will be apparent to one of ordinary skill in the art that many modifications and variations are possible in view of the above teachings, and that by applying knowledge within the skill of the art, one may readily modify and/or adapt for various applications such specific embodiments, without undue experimentation, without departing from the general concept of the present invention. Such adaptations and modifications are intended to be within the meaning and range of equivalents of the disclosed embodiments, based on the teaching and guidance presented herein.

The Detailed Description section is intended to be used to interpret the claims. The Summary and Abstract sections may set forth one or more but not all exemplary embodiments of the present invention as contemplated by the inventor(s), and thus, are not intended to limit the present invention and the claims.

The phraseology or terminology used herein is for the purpose of description and not limitation, such that the terminology or phraseology of the present specification is to be interpreted by the skilled artisan.

The breadth and scope of the present invention(s) should not be limited by any of the above-described exemplary embodiments, but should be defined only in accordance with the claims and their equivalents.

What is claimed is:

1. A needle safety system for use with a syringe, the needle safety system comprising:
   a sleeve defining a guide track and the guide track having-a guide pin retention portion, a travel portion, and a lockout portion;
   a collar configured to be coupled to a portion of the syringe and having-a guide pin radially extending from an exterior surface of the collar,
   a torqueable compression spring that is configured to apply a translational biasing force between the collar and the sleeve and a rotational biasing force between the guide pin and the sleeve preventing movement of the guide pin in a direction opposite to a guide pin biasing direction of the rotational biasing force; and
   a cap that is configured to directly engage with the guide pin to retain the guide pin in the guide pin retention portion of the guide track when the cap is coupled to the sleeve,
   wherein, when the cap is removed from the sleeve, the torqueable compression spring is configured to advance the guide pin into the travel portion of the guide track.

2. The needle safety system of claim 1, wherein the lockout portion and the guide pin retention portion are on opposite sides of the travel portion of the guide track.

3. The needle safety system of claim 1, further comprising a cap seat formed in the sleeve, the cap seat configured to receive a portion of the cap.

4. The needle safety system of claim 1, wherein a retention rib extends from an inner surface of the cap, and
   wherein the retention rib is configured to abut the guide pin to retain the guide pin in the guide pin retention portion.

5. The needle safety system of claim 1, wherein the collar is radially interior of the sleeve.

6. The needle safety system of claim 1, wherein the collar comprises an inner collar and an outer collar rotatably coupled to the inner collar, and wherein the guide pin extends from the outer collar.

7. The needle safety system of claim 6, wherein the outer collar has an accordion portion.

8. The needle safety system of claim 6, wherein the travel portion of the guide track is straight.

9. The needle safety system of claim 1, wherein when the guide pin is in the lockout portion of the guide track, the collar does not move relative to the sleeve.

10. The needle safety system of claim 1, wherein the sleeve comprises a second guide track formed in the sleeve, the second guide track having a second guide pin retention portion, a second travel portion, and a second lockout portion.

11. The needle safety system of claim 10, wherein the guide track and the second guide track are formed on opposite sides of the sleeve.

12. The needle safety system of claim 10, wherein the collar has a second guide pin configured to engage the second guide track.

13. The needle safety system of claim 1, wherein the sleeve comprises a cylindrical portion having a distal end and a proximal end,
   wherein the guide track is provided in the cylindrical portion,
   wherein at least part of the guide track defines a channel in an inner surface of the sleeve at a depth not extending through an entire thickness of the sleeve,
   wherein the guide pin retention portion opens to the travel portion near the proximal end of the cylindrical portion, and
   wherein the lockout portion and the guide pin retention portion are on opposite sides of the travel portion of the guide track.

14. The needle safety system of claim 13, wherein the lockout portion has a capture portion and a channel portion extending from the travel portion to the capture portion.

15. The needle safety system of claim 14, wherein the capture portion includes-a guide pin block configured to retain the guide pin inside the capture portion, wherein the guide pin prohibits relative movement of the sleeve and the collar supporting the guide pin.

16. The needle safety system of claim 15, wherein the cylindrical portion has a longitudinal axis extending between the distal end and the proximal end of the cylindrical portion, and wherein the travel portion of the guide track is straight and is parallel to the longitudinal axis.

17. The needle safety system of claim 15, wherein the guide pin retention portion of the guide track defines a channel configured to receive a retention rib of the cap, and wherein the retention rib is configured to abut the guide pin to retain the guide pin in the guide pin retention portion.

18. The needle safety system of claim 15, wherein the sleeve is assembled from two semi-circular portions.

19. The needle safety system of claim 13, wherein the guide track is formed entirely on the inner surface of the sleeve.

20. The needle safety system of claim 1,
wherein the collar comprises a multi-part collar having an inner collar configured to be coupled to a syringe hub of the syringe and an outer collar rotatably coupled to the inner collar, the guide pin extending from the outer collar,
wherein the sleeve is a cylindrical sleeve and the torqueable compression spring is coupled to the cylindrical sleeve and the outer collar,
wherein the cap includes a retention rib,
wherein the guide pin is configured to be located in the guide pin retention portion and the retention rib is configured to abut the guide pin to retain the guide pin in the guide pin retention portion,
wherein the cylindrical sleeve is configured to extend over a cannula of the syringe when the guide pin is located in the guide pin retention portion, and
wherein a torque imparted by the torqueable compression spring on the multi-part collar and the sleeve is configured to rotate the collar relative to the sleeve to advance the guide pin in the guide track in the guide pin biasing direction into the travel portion of the guide track and to prevent movement of the guide pin in the direction opposite to the guide pin biasing direction.

21. The needle safety system of claim 1, wherein the cap defines a retention rib that is configured to retain the guide pin in the guide pin retention portion of the guide track when the cap is coupled to the sleeve, and
wherein when the cap is removed from the sleeve the torqueable compression spring prevents seating of the cap.

* * * * *